(12) United States Patent
Chmielewski, Jr. et al.

(10) Patent No.: US 7,380,938 B2
(45) Date of Patent: Jun. 3, 2008

(54) APPARATUS TO DETECT AND MEASURE SACCADE AND PUPILARY CHANGES

(75) Inventors: Thomas Adam Chmielewski, Jr., Langhorne, PA (US); James Regis Matey, Levitown, PA (US)

(73) Assignee: Sarnoff Corporation, Princeton, NJ (US)

(*) Notice: Subject to any disclaimer, the term of this patent is extended or adjusted under 35 U.S.C. 154(b) by 571 days.

(21) Appl. No.: 10/809,471

(22) Filed: Mar. 25, 2004

(65) Prior Publication Data

US 2004/0252277 A1  Dec. 16, 2004

Related U.S. Application Data

(60) Provisional application No. 60/457,335, filed on Mar. 25, 2003.

(51) Int. Cl.
*A61B 3/14* (2006.01)
(52) U.S. Cl. .................................................. 351/210
(58) Field of Classification Search ................ 351/209, 351/210, 220, 221
See application file for complete search history.

(56) References Cited

U.S. PATENT DOCUMENTS 5,966,197 A * 10/1999 Yee ........................... 351/210
6,433,326 B1   8/2002 Levine et al.

OTHER PUBLICATIONS

Lawrence Schovanec, Ocular Dynamics and Skeletal Systems, IEEE Control Systmes Magazine, Aug. 2001, pp. 70-79.
FIT Validation Studies, http://www.pmifit.com/validation.htm, Mar. 2, 2004.
Robert J.K. Jakob, "Eye Tracking in Advanced Interface Design," in Virtual Environments and Advanced Interface Dseign, ed. by W. Barfield and T.A. Furness, pp. 258-288, Oxford University Press, New York (1995).
Robert J.K. Jakob, "Eye Movement Based Human Computer Interaction Techniques; Toward Non-Command Interfaces," Advances in Human-Computer Interaction, vol. 4, ed. by H.R. Hartson and D. Hix, pp. 151-190, Ablex Publishing Co., Norwood, N.J. (1993).

* cited by examiner

*Primary Examiner*—Alicia M Harrington
(74) *Attorney, Agent, or Firm*—Lowenstein Sandler PC

(57) ABSTRACT

An eye tracking system employs a first line camera that is configured to track horizontal eye motion and a second line camera that is configured to track vertical eye motion. Output signals from the two line cameras are applied to a processor which identifies and tracks eye motion, using a correlation or edge detection algorithm on boundaries between the sclera, iris and pupil. The system includes multiple controlled light sources and the horizontal and vertical line cameras are configured to track eye motion in response to light stimulus provided by the light sources according to a programmed algorithm. Eye motion for an individual is collected and compared to a model in order to obtain a measure of fitness for the individual. The device may also be used to derive inputs to a computer system based on eye motion or gaze direction.

16 Claims, 3 Drawing Sheets

US 7,380,938 B2

APPARATUS TO DETECT AND MEASURE SACCADE AND PUPILARY CHANGES

This application claims benefit of priority from U.S. provisional application No. 60/457,335 filed Mar. 25, 2003, the contents of which are incorporated herein by reference.

This invention was made with government support under contract number NMA202-97-D-1033 awarded by the Department of the Army. The government has rights in this invention.

FIELD OF THE INVENTION

The present invention concerns a device for tracking eye motion and, in particular, such a device that uses line array imagers.

BACKGROUND OF THE INVENTION

Eye tracking and the measurement of eye response to visual stimulus has applications in many fields including public safety, employee monitoring, computer gaming and computer interfaces for the disabled. It is well known that drug use or alcohol impairs the reaction time of an individual. This reaction time is apparent in the saccades eye movements and in the speed at which the pupils of the impaired person contract.

Saccades are the principal method for moving the eyes to a different portion of a scene. They are sudden, rapid movements of the eyes. While saccades can be initiated voluntarily, once initiated (with a path and terminal point) they must complete the process; thus the path and terminus cannot change "on the fly" during the motion. The delay from stimulus to initial eye motion is in the range of 100-300 ms. Eye motion time is in the range of 30-120 ms and dependent on the angle to be traversed. It is noted that the visual image is suppressed during the saccade, and the retina processes images only during the non-motion time (dwell time) between saccades which may last from 200 to 600 ms.

Pursuit motion can be described as a motion that keeps a moving object foveated (i.e. in the high resolution area of the retina). Contrasted to a saccade motion pursuit motion is smoother and slower. Pursuit motion, however, requires a moving object in the field of vision and cannot be generated voluntarily.

An article by L. Schovanec entitled "Ocular Dynamics and Skeletal systems," IEEE Control Systems Magazine, August 2001, pp 70-79, describes various models of ocular dynamics along with references. For discussion purposes, one eye plant model for horizontal movement can support saccadic, pursuit, vestibular, vergence or optokinetic.

For public safety applications, a measurement of saccadic velocity, pupil diameter, pupil latency constriction, and constriction amplitude are used by the Fit 2000 device, manufactured by Pulse Medical Instruments Inc., to determine whether an individual is "fit for duty.". This device takes a series of measurement including pupilary response and saccadic motion. The system accumulates statistical data from personnel who are deemed fit for duty and, when sufficient measurements have been acquired, it compares new measurements against the stored statistics to determine if the individual falls into or out of the range deemed fit for duty.

This device, however, is rather costly and requires a certain amount of user habituation. In many cases the device will not be able to make measurements if the user does not exactly follow the lights by focusing on a green led either at the left or right. This device measures pupil diameter at a 60 Hz rate while eye position is measured at 600 Hz.

It has also been recognized that eye motion may be used for a computer interface. It may be used as an auxiliary input channel, for example, to replace a pointing device such as a mouse, or it may be used as the primary input device by a disabled person. The use of eye motion as a computer interface is described in an article by R. J. K. Jacob entitled "Eye Movement-Based Human-Computer Interaction Techniques: Toward Non-Command Interfaces," available at the web site of the NEC Research Institute CiteSeer as jacob93eye.html.

The system described in this paper uses a video camera with infrared illumination to track motion of the eye using an image of the cornea plus a "bright-eye" effect generated by a reflection from the retina through the dilated pupil. This apparatus is relatively large and, due to the relatively slow rate of the video camera (e.g. 30 frames per second), may not be able to accurately track eye motion.

SUMMARY OF THE INVENTION

The present invention is embodied in an eye tracking system that employs two line cameras. One line camera is configured to track horizontal eye motion while the other line camera is configured to track vertical eye motion. Output signals from the two line cameras are applied to a processor which tracks an image of the cornea, iris and pupil, using a correlation or edge detection algorithm.

According to one aspect of the invention, system includes multiple controlled light sources and the horizontal and vertical line cameras are configured to track eye motion in response to light stimulus provided by the light sources according to a programmed algorithm.

According to another aspect of the invention, the horizontal camera is configured to track horizontal motion of one eye and the vertical camera is configured to track vertical motion of the other eye.

According to yet another aspect of the invention, the horizontal and vertical cameras each include cylindrical lens elements that expand the range of each of the line cameras in a direction perpendicular to the linear direction of the camera.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
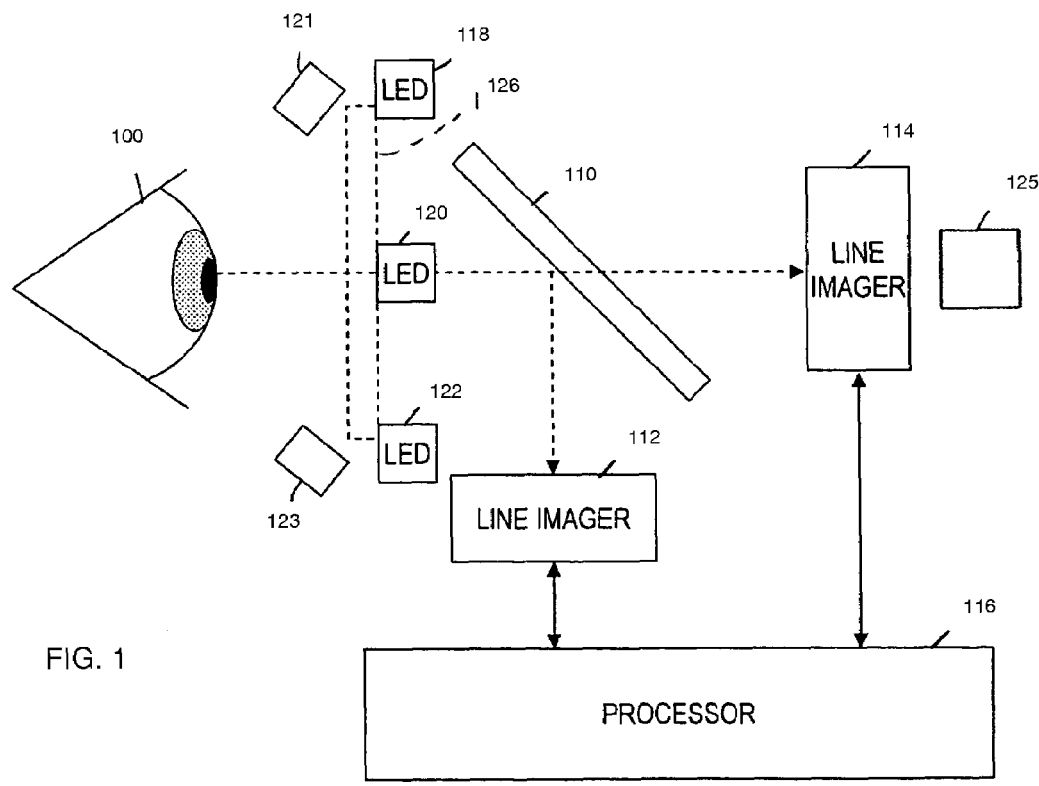
FIG. 1, is a side view functional block diagram of an exemplary eye tracking system according to the present invention.

One exemplary embodiment of the present invention, as shown in FIG. 1, utilizes two line cameras or imagers 112 and 114 and a combination of near Infra-red illuminators 121 and 123 that provide sufficient illumination of the user's eye 100. This exemplary device is a "fit for duty" evaluator that may be used to determine whether users are impaired by monitoring their responses to visual stimuli through their eye movements. Because the eye is not sensitive to infrared radiation, the illuminators 121 and 123 can brightly illuminate the eye without irritating the user. The exemplary system also employs four green (or other color) director LEDs 118, 120, 122 and 124 (shown in FIG. 1A) that are positioned at 12:00, 6:00 and 3:00, 9:00 as viewed by the eye 100. These LEDs are used, as described below, to initiate saccadic motion in defined directions. The exemplary device includes a beam splitter 110 to direct an image of the eye to the horizontal line camera 112 and a processor 116 that interprets the images obtained by the horizontal line camera 112 and the vertical line camera 114. Infrared light reflected from the eye 100 is half passed and half deflected by the beam splitter 110. The exemplary splitter 110 passes approximately half of the light reflected from the eye 100 to the vertical line camera 114 and reflects the other half to the horizontal line camera 112.

Figure 1B:
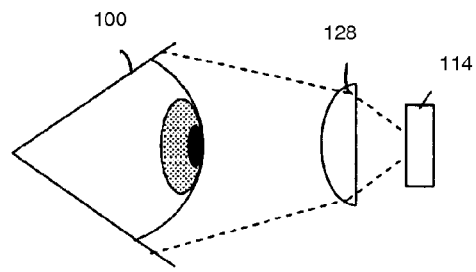
FIGS. 1A and 1B are block diagrams of components of the exemplary eye tracking system shown in FIG. 1.
Figure 1A:
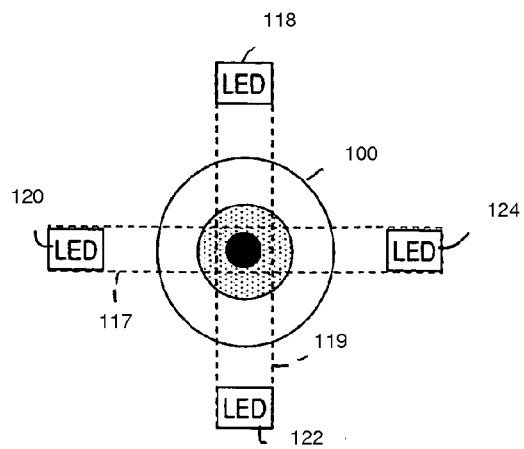

Optionally the four LEDs may be replaced with two "continuous" bar LEDs. 117 and 119 (shown in FIG. 1A). In the exemplary embodiment, bar LED 117 is oriented in the horizontal direction bar LED 119 is oriented in the vertical direction. The LEDs at the ends of the bar 119 may serve the same function as the 12:00 LED 118 and 6:00 LED 122 and the LEDs at the ends of bar 117 may serve the same function as the 9:00 LED 124 and 3:00 LED 120, that is, causing the eye to exhibit saccadic motion. The other LEDs (not separately shown) in the bars 117 and 119 may be used to generate the stimulus for pursuit motion. It is contemplated, however, that other apparatus, for example, a heads-up display 126 may be used in addition to or in place of the LEDs 118, 120, 122 and 124 or the LED bars 117 and 119 to direct the gaze of the user.

As described below, the apparatus shown in FIG. 1, the system may include a visible light source 125, out of the field of view of either of the cameras 112 or 114 but configured to illuminate the eye with visible light. This light source may be used to induce contractions of the iris, causing the size of the pupil to change. In an alternative embodiment, the optional light source 125 may provide near-infrared light to generate a "white eye" effect caused by reflections from the retina in order to make the pupil more visible in the images captured by the line cameras 112 and 114.

An exemplary test sequence for the exemplary fit-for-duty device shown in FIGS. 1 and 1A may involve inducing saccades by first periodically pulsing the LEDs 120 and 124 while monitoring horizontal eye movement, using the imager 112 and processor 116 and then periodically pulsing the LEDs 118 and 112 while monitoring vertical eye movement using the imager 116 and processor 116. As described above, the device may be used on a number of personnel known to be fit for duty in order to generate a frequency distribution of acceptable responses. This frequency distribution may then be modeled as a probability distribution and used to test other personnel to determine if they are fit for duty.

These statistical methods are clearly enhanced with the increase of data, resulting from the ability of the line cameras to sample images faster than a two-dimensional imager, and from the increased spatial resolution of available linear cameras relative to commercial two-dimensional imagers. The problems with these methods remain, however. In particular a credible fit for duty device desirably uses a well established baseline from which to access changes. One exemplary embodiment of the invention uses a combination of statistics and model matching. This embodiment utilizes models of pupilary changes with respect to light intensity and saccadic motion. Data from a particular user at a given test time is matched to a model and depending on the match with respect to previous data or to some norm if there is little or no colleted data for the identified model. The algorithm then identifies those model parameters that are out of normal bounds as defined by the previous data or norm. These parameters provide an indication of a degraded system (i.e. ocular dynamics) and combined with statistics may provide a faster method to obtain a metric of fitness.

The line array imagers 112 and 114 are used so that the sampling rate is not limited by the frame rate of conventional two-dimensional CCD video cameras that can capture images only at a field rate of approximately 16.7 ms. This relatively slow rate allows conventional two-dimensional video cameras to provide only 1 to 7 samples during a saccade. The exemplary imagers 112 and 114 may include analog-to-digital converters (not shown) so that they provide digital signals to the processor 116. Alternatively, the processor 116 may be a microcontroller having internal analog-to-digital converters and the analog signals provided by the imagers 112 and 114 may be applied directly to these digitizing inputs.

The line imagers can operate at higher speeds than the conventional two-dimensional imagers for two reasons. First, there are fewer pixels in the imager to shift each time a sample is taken. Second, by utilizing near infrared illumination, which is invisible to the user and hence non-invasive, the eye can be illuminated at high levels without the user experiencing discomfort. This high level of illumination allows the imagers 112 and 114 to form images of sufficient quality in a very short integration time. It is contemplated that the images provided by the imagers 112 and 114 may be at least a binary images but may also have multibit resolutions (e.g. 4 bits or 8 bits). In this way the sample rate can be made significantly faster than a CCD by between one and two orders of magnitude. The use of two line array cameras or an arrangement of optics and a single line camera allows both horizontal or vertical motion to be monitored. An exemplary line camera that may be used as either of the imagers 112 or 114 is described in U.S. Pat. No. 6,433,326 entitled CMOS/CCD LINE TRANSFER IMAGER WITH LOW DARK CURRENT, the contents of which are incorporated herein by reference for its teaching on CCD line cameras.

Figure 2A:
FIGS. 2A, 2B and 2C are exemplary linear image diagrams derived from one of the line cameras shown in FIG. 1 that are useful for describing the operation of the present invention.
Figure 2B:
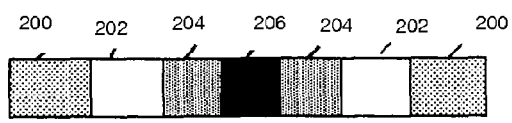
Figure 2C:
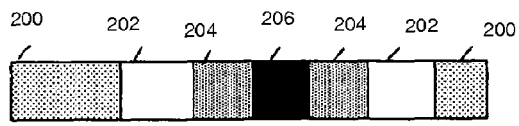

FIGS. 2A, 2B and 2C illustrate exemplary images that may be captured by the horizontal line imager 112. Each of the images shows imaged portions of the eye including the skin 200 surrounding the eye, the sclera 202, the iris 204 and the pupil 206. In these three images, FIG. 2A represents the eye at an initial position and FIGS. 2B and 2C represent successive images as the eye moves from right to left (the image moves from left to right) in response to a stimulus. As can be seen from these images, there are distinct boundaries between the skin 200 and the sclera 202, between the sclera 202 and the iris 204 and between the iris 204 and the pupil 206. Furthermore, these boundaries typically exist on both sides of the pupil.

The exemplary processor 116 processes the samples received from the imagers 112 and 114 using signal/image processing techniques such as a matched filter or edge detector. A particular edge or a combination of multiple edges may be determined for each sample line. This data can then be tracked and processed to obtain the position versus time trajectory which may then be differentiated to obtain velocity, acceleration and jerk profiles. This approach does not rely on Purkinje reflections but rather on measuring the actual pattern of the sclera/iris/pupil. It is contemplated that, using proper filtering, all reflections due to the director diodes 118, 120, 122 and 124 may be eliminated in the image that appears on the CCD array. Because multiple edges may be detected and tracked at a relatively high sample rate, the exemplary embodiment may exhibit relatively high noise immunity. An exemplary filter may be, for example, a color filter that passes only the near infrared light emitted by the illuminators 121 and 123.

The device shown in FIG. 1 is somewhat limited, however, because the eye 100 is desirably limited to substantially horizontal and vertical motion. A diagonal eye movement may be difficult for the device shown in FIG. 1 to process. This is not a problem, however, for a fit-for-duty device, such as is shown in FIG. 1 because the optical stimuli may be mounted on the same axes as the line imagers. The ability to track all types of eye motion may be advantageous, however, for other types of eye sensors, such as a computer input device.

FIG. 1B shows an enhancement to the system shown in FIG. 1 that increases the field of view of the line imager in a direction perpendicular to the line array of the line imager. This enhancement inserts a cylindrical optical element 128 in front of the imager, for example, the horizontal line camera 114. This lens focuses an image of the entire eye and some portion of the skin surrounding the eye on the imager 114. The image is unmodified horizontally but reduced in size vertically. Using this lens in front of both the horizontal and vertical line cameras allows the two cameras to image the entire eye and, thus, track eye motion over its full range. The increased field of view, however, comes with a price, decreased visibility of edges. Because the image of the eye is vertically compressed in this exemplary embodiment, the pixels that include images of the pupil 206 may also include portions of the iris and cornea above and below the pupil. Thus, it may be more difficult for the imagers 112 and 114 to identify and track edges in the resulting linear images. This decrease in the visibility of edges is counterbalanced to some extent by the ability to identify and track multiple edges across the imagers 112 and 114.

Figure 3:
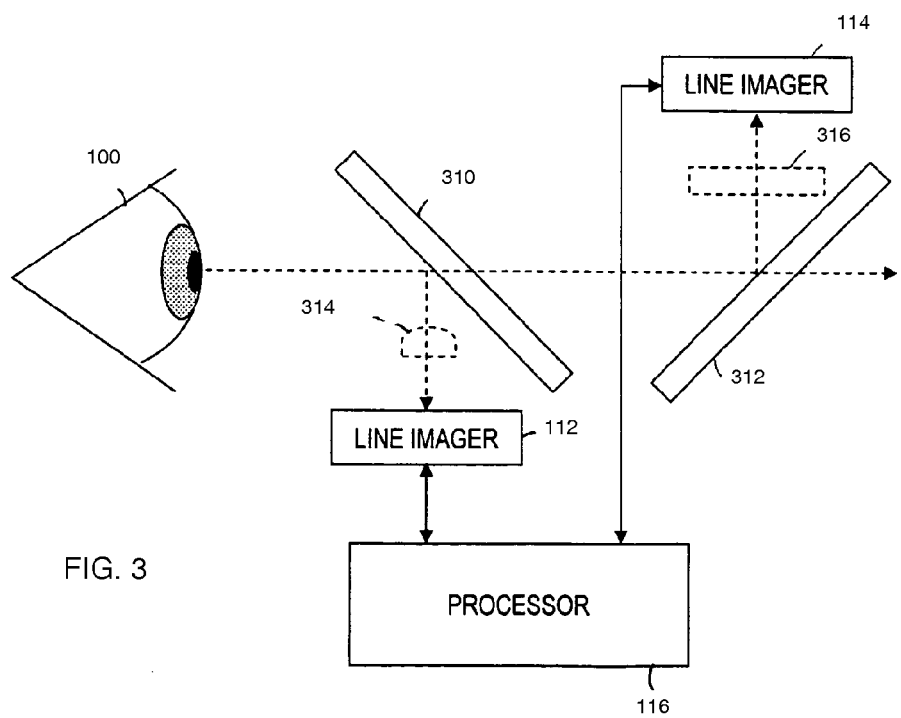
FIGS. 3 and 4 are side view functional block diagrams of alternative exemplary eye tracking systems.

FIG. 3 is a block diagram of another exemplary embodiment of the invention. This embodiment allows a user to see through the device and, thus, may be used as a computer input device. The device is modified from that shown in FIG. 1 by the addition of a second beam splitter 312 that reflects a portion of the infrared light reflected from the eye upward toward the vertical line imager 114. The infrared illuminators 121 and 123 are not shown in FIG. 3 but are used in the exemplary device. Using a device such as that shown in FIG. 3, a user may view items on a computer screen and select an item by simply moving his eye to foveate the object and then focusing on the object for a short time interval. The system can detect the area of the scene at which the viewer is looking either by obtaining Cartesian coordinates from the pupil areas imaged by the horizontal camera 112 and vertical camera 114, by accumulating tracked eye movements from a known reference position or by a combination of these methods.

As shown in FIG. 3, the exemplary computer input device also includes two cylindrical optical elements 314 and 316. The optical element 314 compresses the image of the eye 100 vertically onto the horizontal line imager 112 and the optical element 316 compresses the image of the eye 100 horizontally onto the vertical line imager 114.

In order to allow a maximum amount of light through the device, the exemplary beam splitter 310 may reflect one-quarter of the infrared light to horizontal line imager 112 while the beam splitter 316 reflects one-third of the infrared light to vertical line imager 114 so that the two imagers receive approximately equal amounts of light. The exemplary beam splitters 310 and 312 may be dichroic mirrors that are each tuned to selectively reflect light only at near infrared wavelengths, allowing light in visible wavelengths to pass substantially unattenuated.

Even using these dichroic mirrors, however, it may be distracting for a user to use a system such as that shown in FIG. 3 because of multiple reflections from the mirrors 310 and 312 and the optical attenuation resulting from the two mirrors. These artifacts may be even more pronounced because the user is viewing the image through the device with one eye while looking at it unimpeded with the other eye.

Figure 4A:
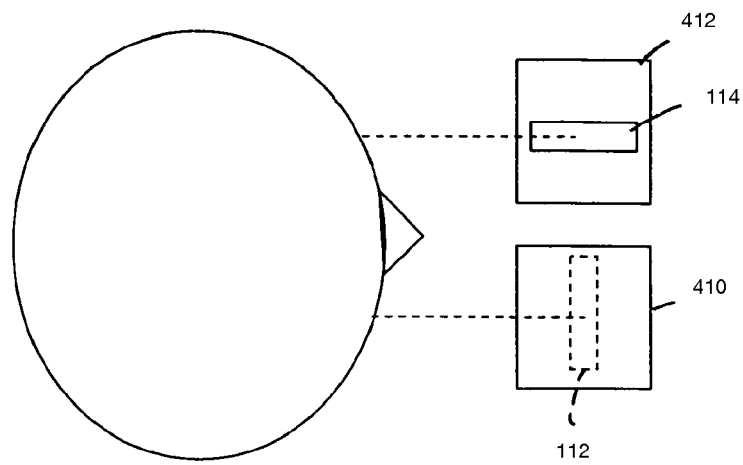
FIG. 4A is a top-view block diagram of a portion of the exemplary eye tracking system shown in FIG. 4.
Figure 4:
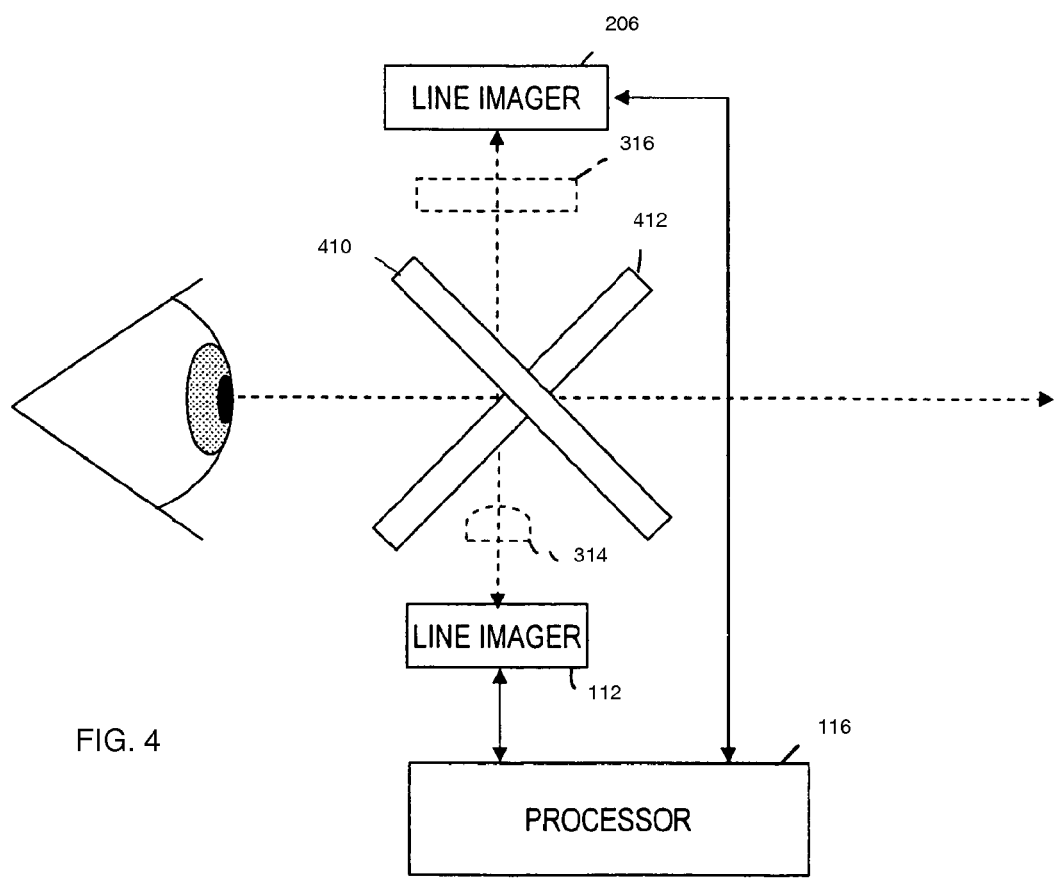

FIGS. 4 and 4A illustrate another embodiment of the invention in which the horizontal image is monitored for one eye while the vertical image is monitored for the other eye. This embodiment makes use of the parallel nature of eye movements when viewing distant objects. This device may be used, for example, as a computer input device for a computer monitor located at normal viewing distance from the user. FIG. 4 shows a side view of portions of the device while FIG. 4A shows a partial top view. The infrared light sources 121 and 123 are used for both eyes in this device but are not shown in FIG. 4 or 4A.

As can be seen from FIG. 4A, near infrared light from the user's right eye is reflected by beam splitter 410 through optional cylindrical optical element 314 onto horizontal line imager 112 while light from the user's left eye is reflected by beam splitter 412 through optional cylindrical optical element 316 onto vertical line imager 114. In this embodiment of the invention, the beam splitters may each reflect one-half of the light or they may be dichroic mirrors that each reflect essentially all of the near infrared light while allowing light at visible wavelengths to pass substantially unattenuated. As in the exemplary apparatus shown in FIGS. 1 and 3, the processor 116 is coupled to receive and process the image data from the two line imagers 112 and 114 to monitor eye motion and determine the gaze direction of the user.

Although the horizontal line imager 112 is shown in the Figures as being below the field of view of the user and the vertical line imager 114 is shown as being either in the field of view or above the field of view, it is contemplated that these imagers may be in other positions. For example, the two imagers may be located on either side of the field of view with appropriate modifications of the mirrors to reflect at least the near infrared light reflected from the eye 100 toward the appropriate imager. In the embodiment shown in FIG. 4, either or both imagers may be located above, below or beside the user's field of view.

Although not shown, it is contemplated that a near infrared illuminator, either one of the illuminators 121 or 123 or an additional illuminator may be used to illuminate the eye on or near the axis formed by the pupil and the fovea to take advantage of the "white eye" effect (similar to red eye of normal film cameras) and have a more delineated image of the pupil area. In this exemplary embodiment, the infrared illuminator may be placed adjacent to one of the line imagers 112 and 114 positioned such that it is out of the field of view of the camera but transmits infrared light toward the eye 100.

Although the system is shown as using a processor 116 to process the signals provided by the imagers 112 and 114, it is contemplated that the processing may occur in either software or hardware and it is conceptually possible for an ASIC or FPGA to replace the processor 116 and, with regard to the embodiment shown in FIG. 1, produce as an output signal some final vector metric such as delay time, time to transit, transit distance, and time constant. In the embodiments shown in FIGS. 3 and 4, the output signal may be a vector indicating a starting gaze direction, a movement vector, an ending gaze direction and a dwell time at the new gaze direction.

It is also contemplated that the exemplary devices may also be used to monitor pupilary stimulus to light by including additional visible light sources (not shown) in the field of view of the eye 100. The use of the line array cameras provides sufficient imaging capability (i.e. image speed and resolution) to obtain position versus time data for changes in the size of the pupil and hence all the derivatives of these changes.

It is also contemplated that data from pupilary and saccadic motion may be combined in the apparatus shown in FIG. 1 to define a more robust fitness index.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An eye tracking system comprising: a horizontal line camera configured to capture a horizontal image of at least a portion of the eye and to provide an output signal representing the horizontal image of the eye; a vertical line camera configured to capture a vertical image of at least a portion of the eye and to provide an output signal representing the vertical image of the eye; a processor, coupled to the horizontal line camera and the vertical line camera to process the signals representing the horizontal and vertical images of the eye to identify and track motion of the eye; and
 a beam splitter configured to reflect a portion of an image of the eye onto one of the horizontal line camera and the vertical line camera and to pass a portion of the image of the eye onto the other one of the horizontal line camera and the vertical line camera.

2. An eye tracking system comprising: a horizontal line camera configured to capture a horizontal image of at least a portion of the eye and to provide an output signal representing the horizontal image of the eye; a vertical line camera configured to capture a vertical image of at least a portion of the eye and to provide an output signal representing the vertical image of the eye; a processor, coupled to the horizontal line camera and the vertical line camera to process the signals representing the horizontal and vertical images of the eye to identify and track motion of the eye; and
 an optical element configured to optically focus an image of the eye onto at least one of the horizontal and vertical line cameras before the image is captured by the at least one of the horizontal line camera and the vertical line camera.

3. An eye tracking system comprising: a horizontal line camera configured to capture a horizontal image of at least a portion of the eye and to provide an output signal representing the horizontal image of the eye; a vertical line camera configured to capture a vertical image of at least a portion of the eye and to provide an output signal representing the vertical image of the eye; a processor, coupled to the horizontal line camera and the vertical line camera to process the signals representing the horizontal and vertical images of the eye to identify and track motion of the eye; and
 multiple controlled visible light sources coupled to the processor, wherein the processor controls the multiple light sources individually to induce eye motion, and the processor further includes a statistical analyzer for comparing the tracked eye motions of a user to eye motion data derived from other users to determine a measure of fitness for the user.

4. An eye tracking system comprising: a horizontal line camera configured to capture a horizontal image of at least a portion of the eye and to provide an output signal representing the horizontal image of the eye; a vertical line camera configured to capture a vertical image of at least a portion of the eye and to provide an output signal representing the vertical image of the eye; a processor, coupled to the horizontal line camera and the vertical line camera to process the signals representing the horizontal and vertical images of the eye to identify and track motion of the eye; and
 a first beam splitter configured to reflect a portion of an image of the eye onto the horizontal line camera; a second beam splitter configured to reflect a portion of the image of the eye onto the vertical line camera; wherein the horizontal and vertical line cameras are configured to be outside of a field of view of the eye and the first and second beam splitters are configured to pass a portion of an image of a scene in the field of view of the eye to the eye.

5. An eye tracking system comprising: a horizontal line camera configured to capture a horizontal image of at least a portion of the eye and to provide an output signal representing the horizontal image of the eye; a vertical line camera configured to capture a vertical image of at least a portion of the eye and to provide an output signal representing the vertical image of the eye; a processor, coupled to the horizontal line camera and the vertical line camera to process the signals representing the horizontal and vertical images of the eye to identify and track motion of the eye; and
 at least one infrared illuminator configured to illuminate the eye as images are being captured by the horizontal and vertical line cameras, the at least one infrared illuminator and the horizontal and vertical line cameras being controlled by the processor to control a rate at which sampled images are obtained from the horizontal and vertical line imagers;
 wherein at least one of the infrared illuminators is configured to illuminate the eye in a direction approximately corresponding to a gaze direction of the eye, whereby the horizontal and vertical images of the illuminated eye exhibit a bright reflection of the at least one infrared illuminator in respective regions of the images corresponding to the pupil of the eye.

6. An eye tracking system comprising: a horizontal line camera configured to capture a horizontal image of at least a portion of the eye and to provide an output signal representing the horizontal image of the eye; a vertical line camera configured to capture a vertical image of at least a portion of the eye and to provide an output signal representing the vertical image of the eye; a processor, coupled to the horizontal line camera and the vertical line camera to process the signals representing the horizontal and vertical images of the eye to identify and track motion of the eye; and a visible light illuminator configured to illuminate the eye as images are being captured by the horizontal and vertical line cameras, the visible light illuminator being controlled by the processor to induce contraction of the iris of the eye; and a pupil size monitor, in the processor, for tracking changes in size of the pupil of the eye in response to illumination of the eye in response to the visible light illuminator.

7. An eye tracking system according to claim 6, wherein the processor further includes: a model of pupilary changes with respect to light intensity and saccadic motion; a comparator which compares saccadic motion and pupilary change data from a user at a given test time to the model and to data derived from other users; a fitness algorithm that identifies data corresponding to specific model parameters that are out of normal bounds as determined from the data derived from other users and, based on the identified parameters determines a metric of fitness for the user.

8. An eye tracking system for tracking eye motion of a user having first and second eyes comprising: a horizontal line camera configured to capture a horizontal image of at least a portion of the first eye of the user and to provide an output signal representing the horizontal image of the first eye; a vertical line camera configured to capture a vertical image of at least a portion of the second eye of the user and to provide an output signal representing the vertical image of the second eye; a processor, coupled to the horizontal line camera and the vertical line camera to process the signals representing the horizontal and vertical images of the eye to identify and track motion of the eye.

9. An eye tracking system according to claim 8, wherein each of the images captured by the horizontal and vertical line cameras includes pixels corresponding to components of the eye including at least two of the sclera, iris and pupil, and the processor includes one of an edge detector and a matched filter to track motion of the eye by identifying corresponding boundaries between respective ones of the components of the eye in successive images provided by the horizontal line camera and the vertical line camera.

10. An eye tracking system according to claim 8 further including: a first beam splitter configured to reflect a portion of an image of the first eye onto the horizontal line camera; and a second beam splitter configured to reflect a portion of an image of the second eye onto the vertical line camera; wherein the horizontal and vertical line cameras are configured to be outside of a field of view of the first and second eyes and the first and second beam splitters are configured to pass a portion of an image of a scene in the field of view of the first and second eyes to the first and second eyes.

11. An eye tracking system according to claim 8, further including: a first optical element configured to optically focus a vertically compressed image of the first eye onto the horizontal line camera; and a second optical element configured to optically focus a horizontally compressed image of the second eye onto the vertical line camera.

12. An eye tracking system according to claim 8 further including multiple controlled visible light sources coupled to the processor, wherein the processor controls the multiple light sources individually to induce eye motion, and the processor further includes a statistical analyzer for comparing the tracked eye motions of a user to eye motion data derived from other users to determine a measure of fitness for the user.

13. An eye tracking system according to claim 8, further including: at least one infrared illuminator configured to illuminate the first and second eyes as images are being captured by the horizontal and vertical line cameras, the at least one infrared illuminator and the horizontal and vertical line cameras being controlled by the processor to control a rate at which sampled images are obtained from the horizontal and vertical line imagers.

14. An eye tracking system according to claim 8, wherein the at least one infrared illuminator is configured to illuminate at least one of the first and second eyes in a direction approximately corresponding to a gaze direction of the eye, whereby at least one of the horizontal and vertical images of the at least one illuminated eye exhibit a bright reflection of the at least one infrared illuminator in respective regions of the images corresponding to the at least one eye.

15. An eye tracking system according to claim 8, further including: a visible light illuminator configured to illuminate at least one of the first and second eyes as images are being captured by the horizontal and vertical line cameras, the visible light illuminator being controlled by the processor to induce contraction of the iris of the at least one eye; and a pupil size monitor, in the processor, for tracking changes in size of the image of the pupil of the at least one eye in response to illumination of the at least one eye in response to the visible light illuminator.

16. An eye tracking system according to claim 8, wherein the processor further includes: a model of pupilary changes with respect to light intensity and saccadic motion; a comparator which compares saccadic motion and pupilary change data from a user at a given test time to the model and to data derived from other users; a fitness algorithm that identifies data corresponding to specific model parameters that are out of normal bounds as determined from the data derived from other users and, based on the identified parameters determines a metric of fitness for the user.

* * * * *